United States Patent
Franko-Filipasic et

[11] 3,986,882
[45] Oct. 19, 1976

[54] FLAME RETARDANT REGENERATED CELLULOSE FILAMENTS CONTAINING POLYMERIC PHOSPHAZENES

[75] Inventors: Borivoj Richard Franko-Filipasic, Morrisville, Pa.; John Francis Start, Mercerville, N.J.

[73] Assignee: FMC Corporation, Philadelphia, Pa.

[22] Filed: Nov. 12, 1973

[21] Appl. No.: 414,981

Related U.S. Application Data

[62] Division of Ser. No. 230,954, March 1, 1972, Pat. No. 3,840,621.

[52] U.S. Cl. ............................... 106/15 FP; 106/168
[51] Int. Cl.$^2$ ............................................. C09J 5/18
[58] Field of Search ............... 106/15 FP, 168, 177; 260/927 N, 2 P; 117/138, 136

[56] References Cited
UNITED STATES PATENTS

| | | | |
|---|---|---|---|
| 2,192,921 | 3/1940 | Lipkin | 260/927 N |
| 2,866,773 | 12/1958 | Redfarn | 260/2 P |
| 2,909,446 | 10/1959 | Redfarn et al. | 117/138 |
| 3,164,556 | 1/1965 | Apley | 260/2 |
| 3,455,713 | 7/1969 | Godfrey | 106/165 |
| 3,532,526 | 10/1970 | Godfrey | 106/165 |

FOREIGN PATENTS OR APPLICATIONS

| | | | |
|---|---|---|---|
| 1,381,023 | 1/1964 | France | 260/927 |

*Primary Examiner*—Theodore Morris

[57] ABSTRACT

Regenerated cellulose filaments having dispersed therein a flame-retardant amount of phosphonitrilic esters containing a substantial amount of cyclic structures, dimerized, oligomerized, or polymerized, that are prepared by esterification of a phosphonitrilic chloride polymer with ethylene glycol.

6 Claims, No Drawings

FLAME RETARDANT REGENERATED CELLULOSE FILAMENTS CONTAINING POLYMERIC PHOSPHAZENES

This is a division of application Ser. No. 230,954, filed Mar. 1, 1972, now U.S. Pat. No. 3,840,621.

This invention relates to regenerated cellulose filaments flame retarded with phosphazene compounds. The phosphazene compounds are phosphonitrilic esters containing a substantial amount of cyclic structures dimerized or oligomerized by esterification of a phosphonitrilic chloride with ethylene glycol.

It is desirable, for many textile purposes, to provide cellulose fibers and yarns having greatly decreased flammability. In the manufacture of rayon by the viscose method, rayon has been made permanently flame-retardant by dispersing in the rayon a flame-retardant amount of a substantially water-insoluble, liquid, phosphonitrilic polymer as disclosed by Godfrey in U.S. Pat. Nos. 3,455,713, 3,505,087, and 3,532,526 issued July 15, 1969, Apr. 7, 1970, and Oct. 6, 1970. These phosphonitrilic polymers are conventionally made by esterifying a predominately trimeric chlorophosphazene (phosphonitrilic chloride polymer). A predominately cyclic chlorophosphazene can be made by bringing into contact elemental chlorine, phosphorus trichloride and ammonium chloride in an inert solvent at reflux temperatures as described in U.S. Pat. Nos. 3,359,080 and 3,462,247 issued Dec. 19, 1967, and Aug. 19, 1969, respectively.

Although the Godfrey compositions do not seriously degrade rayon fiber properties, it is always desirable to have more effective flame retardants allowing attainment of adequate flame retardance at a lower additive level with a consequent lowered impairment of physical properties of the rayon fibers and a decrease in cost. Recently, it has been discovered that phosphonitrilates of increased viscosity are improved flame retardants for rayon. Thus, it is highly desirable to provide processes for making phosphonitrilates having enhanced flame-retardant effects in rayon.

In accordance with the present invention, there is provided regenerated cellulose filaments and filamentary articles having dispersed therein substantially water-insoluble, polymeric phosphonitrilates containing a substantial amount of cyclic structures dimerized or polymerized by esterification of a phosphonitrilic chloride polymer with ethylene glycol. These dimerized or polymerized phosphonitrilic esters, also termed phosphonitrilates, are fluids of unusually high viscosity and molecular weights and they are exceptionally useful for making permanently flame-retarded rayon. These phosphonitrilates are used to flame retard regenerated cellulose in amounts of 1–25% by weight based on the cellulose. One such phosphonitrilate has a structure represented as:

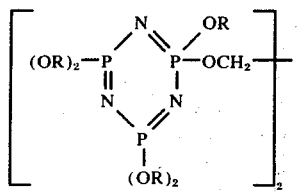

in which R is a lower alkyl or alkenyl radical containing 1–6 carbon atoms.

Phosphonitrilate esters are made by first preparing a chlorophosphazene or phosphonitrilic chloride by a conventional process as described in U.S. Pat. Nos. 3,359,080 and 3,462,247 issued Dec. 19, 1967, and Aug. 19, 1969, respectively, which comprises bringing in contact elemental chlorine, phosphorus trichloride and ammonium chloride in an inert solvent at reflux temperature, the ammonium chloride being present at any time during the reaction in a proportion at least equal molar with the phosphorus trichloride. The chlorophosphazenes are reacted with a low molecular weight glycol, such as ethylene glycol, propylene glycol, and the like, which is used as a coupling agent. This results in coupling and esterification of the chlorophosphazenes to produce esters of greatly increased viscosity. Where desired, esterification is not complete. Conventional esterification procedures can be used to complete the esterification, such as reaction of the residual chloride atoms with an alcohol, alkoxide or alkylene oxides.

Conventional chlorophosphazenes can be crosslinked with lower glycols containing 1 to 6 carbon atoms with ethylene and propylene glycol being preferred. Reaction with the glycol connects the chlorophosphazene molecules. When complete esterification does not result from reaction with the glycols, alkyl alcohols, sodium alkoxide and alkylene oxides can be used to complete esterification. The alkyl and alkenyl portions are generally those containing 1 to 6 carbon atoms, and include such radicals as ethyl, 2-chloroethyl, methyl, n-propyl, isopropyl, butyl, isobutyl, amyl, isoamyl, hexyl, allyl and crotyl groups. Amines such as triethyl amine to form amine hydrochloride are used for ease in handling and processing and are not part of the invention.

The phosphonitrilic chloride polymer used in this invention is a cyclic trimer, tetramer or higher cyclic polymer, or a linear polymer and is preferably employed as a mixture of these isomers based on economy and similar performance to the pure compound. The lowest possible temperatures conducive to efficient processing are used. Temperatures of 80° to 120° C can be used. However, it is preferred to use temperatures of 90° to 105° C with the lower temperatures of 90°–100° C being preferred.

These esterifications are rapid and exothermic. The time of the reaction is controlled by the ability of the reaction vessel to remove the exothermic heat when there is a moderate rate of diluent reflux.

The fluids, diluents or solvents used in the process of this invention are inert to the reaction mass, capable of reflux at temperatures over 100° C and easily removed by distillation. Aromatic solvents such as toluene or paraffinic solvents such as octane are preferred.

The reactant ratios are carefully controlled in order to achieve the desired physical characteristics in the fluid product. The preferred reactant ratios are 5 to 10 moles of phosphonitrilic chloride per mole of glycol. The most preferred reactant ratio is about 8 moles of phosphonitrilic chloride per mole of glycol.

The following examples further illustrate this invention. All proportions in the specification and in the examples are by weight unless otherwise noted.

EXAMPLE 1

Increasing the molecular weights and consequently the viscosities of the flame-retardant fluids by coupling or cross-linking with ethylene glycol either during or previous to propyl ester formation is demonstrated. Essentially pure trimer of phosphonitrilic chloride, $(PNCl_2)_3$, was prepared (by fractional crystallization) and reacted as follows: To a solution of 11.6 gms of $(PNCl_2)_3$ in 50 ml of toluene was charged slowly with agitation 1.03 gms (0.0166 mole) of ethylene glycol dissolved in 6 gms (0.0595 mole) of triethylamine. The solution was agitated for 30° minutes at 100° C and cooled slowly. The solid amine hydrochloride was removed by filtration and the filtrate was charged to sodium propoxide in toluene at reflux. The ester was obtained by water-washing the crude mixture and concentrating the dried organic layer. The desired compound was the ethylene glycol ester of bis-pentapropoxycyclotriphosphazatriene. The product was obtained in 78.8% yield as a viscous liquid, refractive index 1.4696 at 22° C, acid number 11.5, viscosity 6075 centistokes at 25° C. The molecular weight by vapor phase osmometry was 1088 (920.8 calculated for the bis ester). Elemental analysis, nitrogen = 9.14% found, 9.12% calculated; phosphorus = 20.86 found, 20.18 calculated; chlorine = 0.31% found, 0 calculated.

EXAMPLE 2

The preparation of Example 1 was repeated with cyclic, hexane soluble $(PNCl_2)_3$ mixture, 25 gms; ethylene glycol, 1.55 gms; triethylamine, 10 ml; all in 100 ml of toluene solution. Isolation of the glycol ester and further complete esterification with sodium propoxide yielded 75% of a viscous fluid refractive index 1.4700 at 23° C, a molecular weight of 982, and a viscosity of 3285 centistokes at 25° C.

EXAMPLE 3

Cyclic, hexane soluble phosphonitrilic chloride, principally $(PNCl_2)_3$, 25 gms; ethylene glycol, 1.7 gms; triethylamine, 10 gms; all in 100 ml of toluene were utilized. The ester was isolated and esterified further and completely with sodium propoxide. There was obtained a viscous fluid in 85% yield, refractive index 1.4703 at 24° C, a molecular weight of 751 and a viscosity of 720 centistokes at 25° C.

EXAMPLE 4

To illustrate the use of ethylene glycol during the formation of propyl esters, a solution of 78 ml of n-propanol and 3.6 gms of ethylene glycol were charged to a mixture of 18 gms molten sodium metal dispersed in 225 ml of toluene at 102 to 105° C. The mixture was refluxed with agitation for 30 minutes to insure complete reaction. A solution of 38.3 gms of cyclic phosphonitrilic chloride, principally $(PNCl_2)_3$, mixture in toluene solution was added slowly to the refluxing mixture. Heating was continued for 5½ hours during which time samples were withdrawn every 30 minutes and analyzed for unreacted chloride. When the chloride level was 0.1%, the reaction mixture was cooled and washed with tap water to dissolve the salts. The organic layer was separated, dried, and concentrated in vacuo. There was obtained a viscous fluid of the following physical properties:

| | |
|---|---|
| Average molecular weight | 1100 |
| Viscosity (centistokes at 25° C) | 2175 |
| Refractive index at 24° C | 1.4674 |

Elemental analyses follow:

| | Found | Calculated for $PN(OR)_2$; R=propyl |
|---|---|---|
| C | 39.43 | 44.17 |
| H | 7.41 | 8.65 |
| N | 8.87 | 8.58 |
| P | 20.11 | 18.98 |
| Cl | 0.08 | 0.00 |

EXAMPLE 5

The phosphorus-containing products of Example 4 and a flame-retardant compound as described in the Example of the Godfrey U.S. Pat. No. 3,455,713 were evaluated for their flame-retardant effect in rayon yarn produced from a filament-forming viscose comprising 8.6 wt.% cellulose, 6.2 wt.% sodium hydroxide and 33.0% carbon disulfide, based on the weight of the cellulose, and having a viscosity at spinning of 6000 centipoises at 18° C. The phosphorus-containing flame-retardant compounds were injected into the viscose stream at the desired rate based on the weight of the cellulose in the viscose and the viscose mixture passed through a high shear blender. This provided a viscose having the flame retardant dispersed therein as fine liquid particles of from 1 to 10 microns in size.

Viscoses prepared as described above and containing deliberately varied amounts of the phosphorus-containing flame-retardant compounds were spun into conventional aqueous acid spin baths comprising 9.8 wt.% sulfuric acid, 3.0 wt.% zinc sulfate and 17.5 wt.% sodium sulfate at a bath temperature of 50° C. The yarn was wet stretched about 35% of its original length. Yarns having a denier of 240 and 40 filaments were processed by passing them through a series of baths including water wash, desulfurization, bleach, bleach acid, antichlor, and soft finish bath. The yarns were dried, transferred to packages, and finally knit into circular knit fabrics. The regenerated cellulose yarns prepared in this manner were made up of individual filaments having fine liquid flame-retardant particles locked in the cellulose matrix.

Assays of the flame retardant in the fabrics were made by determining the phosphorus content of the neat flame retardants and the fabrics.

The table sets forth the weight amount of flame retardant in the conditioned fabric, the weight amount of phosphorus in the dry regenerated cellulose fabric, and the percent of flame retardant retained in the finished fabric compared to the amount originally injected into the viscose. The amount of phosphorus in the dry fabric was used to calculate the amount of flame retardant present in the conditioned fabric. The control flame retardant was that described in the Example of U.S. Pat. No. 3,455,713 and consisted of a liquid mixture of di-n-propyl phosphonitrilate polymers including about 65% trimer, 15% tetramer, between about 15 and 20% of higher cyclic polymers and less than about 5% of linear polymers.

Flammability testing was made by employing the (1) Limited Oxygen Index (LOI) method and (2) the Vertical Strip Test AATCC34-1969.

The LOI test is made by supporting a 3×8 inch conditioned fabric sample in a U-shaped frame which is mounted in a cylindrical open chamber. Controlled mixtures of oxygen and nitrogen gases are admitted into the base of the chamber and allowed to displace the normal atmosphere. When an equilibrium atmosphere in the chamber is obtained, the fabric sample is ignited with a butane gas flame by contacting the flame to the top edge of the fabric. If the fabric fails to ignite, the oxygen ratio of the atmosphere is increased to a level where the flame will just propagate. Conversely, if the fabric ignites and the flame propagates, the oxygen ratio of the atmosphere is reduced to a level where flame propagation is virtually zero. The LOI is the minimum percentage concentration of the oxygen atmosphere in which the test fabric will ignite and permit flame propagation. A control rayon fabric has an LOI of 18.5.

The vertical strip test is made by supporting a 3×10 inch fabric sample in a U-shaped frame which exposes 2×10 inch fabric. The sample and frame is supported vertically in a draft-free chamber with the open end of the fabric frame pointed down. Ignition of the fabric is made with a Tirrell Burner fueled with butane. A 1½ inch long flame is aligned to the base of the fabric so that ¾ inch of the flame bites into the fabric. Flame contact time is for (a) 3 seconds and (b) 12 seconds. Data are obtained to show the length of the char and the time of after flame.

The table also sets forth the results of the above described flammability tests carried out on the fabric samples. It should be borne in mind that the tests were made using knitted fabrics of relatively light construction. The vertical flame-retardant test results are useful for a relative appraisal of the fabrics tested as this test is greatly affected by fabric weight. In the vertical test, five samples are tested, the average char length must be less than 7 inches to pass and one char of 10 inches fails the test.

The limited oxygen test data have greater relevance to the flammability of normal apparel weight fabrics since the limited oxygen indices are not dependent on fabric weight.

at a temperature of 80 to 120° C a phosphonitrilic chloride having the general formula:

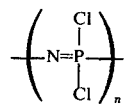

in which $n$ is at least 3 with both (a) a low molecular weight alkylene glycol containing 1 to 6 carbon atoms and (b) alkyl alcohols containing 1 to 6 carbon atoms, sodium alkoxides containing 1 to 6 carbon atoms or alkylene oxides containing 2 to 6 carbon atoms, wherein the reactant ratio is one mole of glycol per 5 to 10 moles of phosphonitrilic chloride.

2. The product of claim 1 in which the glycol is ethylene glycol or propylene glycol.

3. The product of claim 1 in which the phosphonitrilic chloride polymer is first reacted with the lower glycol to form a partially esterified product and the partially esterified product is further esterified with alkyl alcohols, sodium alkoxides containing 1 to 6 carbon atoms or alkylene oxides containing 2 to 6 carbon atoms.

4. The regenerated cellulose filaments of claim 1 containing 1 to 25%, based on the weight of the cellulose, of the liquid polymeric phosphazene.

5. The regenerated cellulose filaments of claim 1 in which the alkyl portion of the alkyl alcohols and sodium alkoxides may be methyl, ethyl, chloroethyl, propyl, isopropyl, butyl, isobutyl, amyl, isoamyl, hexyl, allyl or crotyl radicals.

6. A method of preparing a flame-retardant regenerated cellulose filament which comprises mixing viscose and a flame retardant amount of a substantially water-insoluble liquid polymeric phosphazene made by esterifying at a temperature of 80° to 120° C a phosphonitrilic chloride having the general formula:

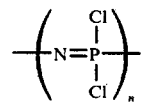

in which $n$ is at least 3 with both (a) a low molecular

TABLE

| Flame Retardant (FR) | Fabric Sample No. | % FR in Conditioned Fabric | % P | Limited Oxygen Index Test | Vertical Flame Test | | | |
|---|---|---|---|---|---|---|---|---|
| | | | | | 3 Sec. | | 12 Sec. | |
| | | | | | Char Length, In.* | After Flame, Sec. | Char Length, In. | After Flame, Sec. |
| Example 4 | 1 | 5.6 | 1.17 | 25.3 | 10.0(F) | 15.6 | 10.0(F) | 4.2 |
| | 2 | 9.2 | 1.91 | 26.4 | 10.0(F) | 14.2 | 6.9 | NAF** |
| | 3 | 11.7 | 2.43 | 26.4 | 10.0(F) | 14.6 | 5.8 | NAF |
| Control | 1 | 5.0 | 0.98 | 23.8 | 10.0 | 18.0 | 10.0 | 7 |
| | 2 | 9.9 | 2.11 | 25.7 | 10.0 | 17.0 | 9.0 | NAF-5.0 |
| | 3 | 11.0 | 2.30 | 24.7 | 10.0 | 17.2 | 9.0 | NAF-7.7 |
| | 4 | 14.1 | 2.90 | 25.3 | 9.0 | 13.0 | 5.6 | NAF |
| | 5 | 16.9 | 3.50 | 26.0 | 3.0 | NAF-4.5 | 5.2 | NAF |
| | 6 | 21.0 | 4.30 | 26.3 | 1.9 | NAF | 5.2 | NAF |

*Over 7 inches fails in the three second test.
**NO AFTER FLAME
(F)Failed

What is claimed is:

1. Regenerated cellulose filaments and filamentary articles, said filaments having dispersed therein a flame-retardant amount of a substantially water-insoluble, liquid polymeric phosphazene made by esterifying weight glycol containing 1 to 6 carbon atoms and (b) alkyl alcohols containing 1 to 6 carbon atoms, sodium alkoxides containing 1 to 6 carbon atoms or alkylene oxides containing 2 to 6 carbon atoms, wherein the reactant ratio is one mole of glycol per 5 to 10 moles of phosphonitrilic chloride.

* * * * *